US010357143B2

(12) United States Patent
Koyama et al.

(10) Patent No.: US 10,357,143 B2
(45) Date of Patent: Jul. 23, 2019

(54) ENDOSCOPE

(71) Applicant: OLYMPUS CORPORATION, Hachioji-shi, Tokyo (JP)

(72) Inventors: Reiji Koyama, Tachikawa (JP); Shohei Uehara, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 68 days.

(21) Appl. No.: 15/432,474

(22) Filed: Feb. 14, 2017

(65) Prior Publication Data

US 2017/0150870 A1 Jun. 1, 2017

Related U.S. Application Data

(63) Continuation of application No. PCT/JP2015/074228, filed on Aug. 27, 2015.

(30) Foreign Application Priority Data

Sep. 5, 2014 (JP) ................................ 2014-181738

(51) Int. Cl.
*A61B 1/00* (2006.01)
*A61B 1/005* (2006.01)
*A61B 1/012* (2006.01)
*A61B 1/015* (2006.01)
(Continued)

(52) U.S. Cl.
CPC ........ *A61B 1/00066* (2013.01); *A61B 1/0051* (2013.01); *A61B 1/0052* (2013.01);
(Continued)

(58) Field of Classification Search
CPC ............ A61B 1/00064; A61B 1/00066; A61B 1/00068; A61B 1/00112; A61B 1/00119; A61B 1/00128; A61B 1/00105; A61B 1/0011; A61B 1/005; A61B 1/012; A61B 1/015; A61B 1/018; A61B 1/126;
(Continued)

(56) References Cited

U.S. PATENT DOCUMENTS

2004/0193011 A1\* 9/2004 Akiba .................. A61B 1/0011
600/122

FOREIGN PATENT DOCUMENTS

JP    H09-206276 A    8/1997
JP    2000-051148 A    2/2000
(Continued)

OTHER PUBLICATIONS

Jul. 19, 2016 Office Action issued in Japanese Patent Application No. 2015-560445.
(Continued)

*Primary Examiner* — Ryan N Henderson
(74) *Attorney, Agent, or Firm* — Oliff PLC (57) ABSTRACT

An endoscope includes a plate member to which a member be operated to bend a bendable portion is fixed and which includes a through hole, and a tubular unit formed in a tubular shape to make a fluid flow and including a coupling portion which functions as a protruding portion disposed so as to be protruded from an outer surface. The endoscope further includes a positioning mechanism which positions the plate member and the tubular unit relative to each other so as to dispose the protruding portion around a periphery of the through hole including the through hole.

5 Claims, 6 Drawing Sheets

(51) Int. Cl.
    *A61B 1/018*       (2006.01)
    *A61B 17/00*      (2006.01)
    *A61M 25/01*     (2006.01)

(52) U.S. Cl.
    CPC ...... *A61B 1/00064* (2013.01); *A61B 1/00121* (2013.01); *A61B 1/00128* (2013.01); *A61B 1/012* (2013.01); *A61B 1/015* (2013.01); *A61B 1/018* (2013.01); *A61M 25/0133* (2013.01); *A61M 25/0136* (2013.01); *A61B 2017/003* (2013.01); *A61B 2017/00318* (2013.01)

(58) Field of Classification Search
    CPC ... A61B 2017/003; A61B 2017/00318; A61M 25/0133; A61M 25/0136
    See application file for complete search history.

(56) References Cited

FOREIGN PATENT DOCUMENTS

| | | | | |
|---|---|---|---|---|
| JP | 2001-046329 A | | 2/2001 | |
| JP | 2001057960 A | * | 3/2001 | ............. A61B 1/005 |
| WO | 2014/109099 A1 | | 7/2014 | |

OTHER PUBLICATIONS

Oct. 13, 2015 International Search Report issued in International Patent Application No. PCT/JP2015/074228.
Mar. 15, 2016 Office Action issued in Japanese Patent Application No. 2015-560445.

\* cited by examiner

ENDOSCOPE

CROSS-REFERENCE TO RELATED APPLICATIONS

This application is a Continuation Application of PCT Application No. PCT/JP2015/074228, filed Aug. 27, 2015 and based upon and claiming the benefit of priority from prior Japanese Patent Application No. 2014-181738, filed Sep. 5, 2014, the entire contents of all of which are incorporated herein by reference.

BACKGROUND OF THE INVENTION

1. Field of the Invention

The present invention relates to an endoscope configured to relatively position a plate member to which a member for operating to bend a bendable portion of an endoscope is fixed and a tubular unit in which a fluid flows.

2. Description of the Related Art

For example, the endoscope disclosed in Jpn. Pat. Appln. KOKAI Publication No. 2000-51148 includes a positioning mechanism which relatively positions a plate member to which a member for operating to bend a bendable portion of the endoscope is fixed and a tubular unit in which a fluid flows. The positioning mechanism has a cylindrical main body member. The main body member has a distal end portion on which a proximal end portion of a bending prevention portion of the endoscope is externally mounted and a proximal end portion on which a distal end portion of a holding casing disposed on an operation portion of the endoscope is externally mounted. For example, the plate member is manufactured by die casting so as to ensure the strength of the plate member. The plate member has a distal end portion fixed to the proximal end portion of the main body member with screws. The tubular unit is fixed to the main body member through a branched tube member.

This branched tube member has one distal end portion and two proximal end portions formed in a bifurcated shape. The branched tube member couples a treatment instrument insertion tube portion which is coupled to the distal end portion of the branched tube member to a mouth ring member which is coupled to a first proximal end portion of the branched tube member, and forms a path to a treatment instrument insertion port portion. The branched tube member couples the treatment instrument insertion tube portion to the tubular unit coupled to a second proximal end portion of the branched tube member.

In general, in the endoscope, the bending operation portion is operated with a left hand while grasping the endoscope with the left hand. At this time, a treatment instrument inserted from the treatment instrument insertion port portion into the inside of the endoscope is operated with a right hand. The bending operation portion and the treatment instrument insertion port portion are disposed in consideration of this graspability and two types of operability. More specifically, the bending operation portion is disposed on a right side surface of the endoscope when viewed from an operator who grasps the endoscope, while the treatment instrument insertion portion is disposed between the right side surface and a back surface of the endoscope when viewed from the operator. In this manner, the bending operation portion and the treatment instrument insertion portion are positioned relative to each other. For this reason, the plate member and the tubular unit are positioned based on the positional relationship between the bending operation portion and the treatment instrument insertion port portion described above. Therefore, the branched tube member, the treatment instrument insertion tube portion, and the mouth ring member are disposed on an obverse surface side of the plate member. The tubular unit extends from the obverse surface side to the reverse surface side of the plate member through a lengthwise-direction recess portion disposed in a distal end of the plate member. The lengthwise-direction recess portion is disposed along a lengthwise direction of the plate member so as to penetrate through the plate member in its thickness direction. In this manner, the branched tube member, the treatment instrument insertion tube portion, and the mouth ring member are disposed on the opposite side of the plate member to the tubular unit.

BRIEF SUMMARY OF THE INVENTION

An aspect according to an endoscope includes a plate member to which a member configured to operate to bend a bendable portion of the endoscope is fixed and which includes a through hole; a tubular unit formed in a tubular shape to make a fluid flow and including a protruding portion disposed so as to be protruded from an outer surface of the tubular unit; and a positioning mechanism configured to position the plate member and the tubular unit relative to each other so as to dispose the protruding portion around a periphery of the through hole including the through hole.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described in detail below with reference to the accompanying drawings.

[First Embodiment]
[Configuration]

An embodiment will be described with reference to FIGS. 1, 2, 3A, 3B, 3C, and 3D. For the sake of illustrative clarity, some drawings omit illustrations of some members.

[Endoscope 10]

Figure 1:
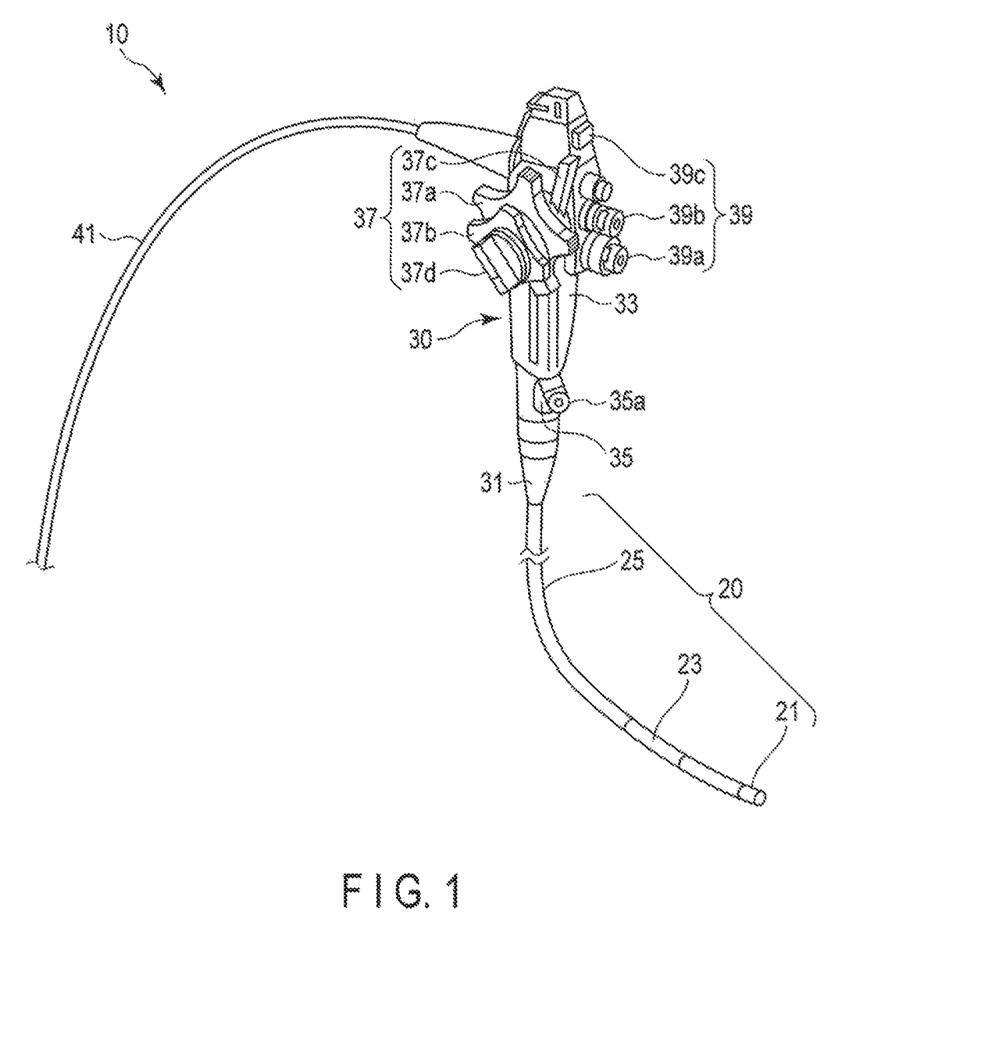
FIG. 1 is a schematic view of an endoscope according to an embodiment of the present invention.

An endoscope 10 shown in FIG. 1 is a direct-viewing endoscope or side-viewing endoscope. The endoscope 10 according to this embodiment will be described as, for example, a medical endoscope, however, this is not limited. The endoscope 10 can be suitably used as an industrial endoscope as well as a medical endoscope.

As shown in FIG. 1, the endoscope 10 includes a hollow elongated insertion portion 20 which is inserted into a lumen such as a body cavity in a patient, and an operation portion 30 which is coupled to a proximal end portion of the insertion portion 20 and operates the endoscope 10.

[Insertion Portion 20]

As shown in FIG. 1, the insertion portion 20 includes a distal hard portion 21, a bendable portion 23, and a flexible tube portion 25 disposed in this order from a distal end portion side of the insertion portion 20 to the proximal end portion side of the insertion portion 20. A proximal end portion of the distal hard portion 21 is coupled to a distal end portion of the bendable portion 23, a proximal end portion of the bendable portion 23 is coupled to a distal end portion of the flexible tube portion 25.

[Operation Portion 30]

As shown in FIG. 1, the operation portion 30 includes a bending prevention portion 31 from which the flexible tube portion 25 extends, a grasping portion 33 which is coupled to a proximal end portion of the bending prevention portion 31, and grasped by an operator who operates the endoscope 10, and a universal cord 41 which is connected to the grasping portion 33.

[Grasping Portion 33.]

As shown in FIG. 1, the grasping portion 33 includes a treatment instrument insertion portion 35 in which a treatment instrument is disposed to be inserted into the endoscope 10, a bending operation portion 37 which is operated to bend the bendable portion 23, and a switching portion 39. The treatment instrument insertion portion 35 is disposed on a distal end portion side of the grasping portion 33, the bending operation portion 37 and the switching portion 39 are disposed on a proximal end portion side of the grasping portion 33.

[Treatment Instrument Insertion Portion 35]

The treatment instrument insertion portion 35 branches with respect to the grasping portion 33. For this reason, as shown in FIG. 1, a central axis direction of the treatment instrument insertion portion 35 is tilted with respect to a central axis direction of the grasping portion 33.

As shown in FIG. 1, the treatment instrument insertion portion 35 includes a treatment instrument insertion port portion 35a which is disposed in an end portion of the treatment instrument insertion portion 35 to allow a treatment instrument to be inserted into the endoscope 10.

As shown in FIG. 1, a central axis of the treatment instrument insertion port portion 35a is coaxially disposed along the central axis of the treatment instrument insertion portion 35 and is tilted with respect to the central axis of the grasping portion 33. In addition, the central axis direction of the treatment instrument insertion port portion 35a is tilted with respect to the central axis direction of the grasping portion 33.

[Bending Operation Portion 37]

As shown in FIG. 1, the bending operation portion 37 includes a first operation knob 37a which bends the bendable portion 23, for example, up and down, and a second operation knob 37b which bends the bendable portion 23, for example, right and left. The bending operation portion 37 further includes a first fixing knob 37c which fixes the vertical position of the bendable portion 23 and a second fixing knob 37d which fixes the horizontal position of the bendable portion 23. The bending operation portion 37 is operated by a finger of a left hand when grasping the grasping portion 33 with the left hand.

[Switching Portion 39]

As shown in FIG. 1, the switching portion 39 includes a suction switch 39a, an air-supply/water-supply switch 39b, and various types of switches 39c for endoscope imaging. The suction switch 39a, the air-supply/water-supply switch 39b, and the various types of switches 39c is operated by a finger of the left hand when grasping the grasping portion 33 with the left hand.

[Universal Cord 41]

As shown in FIG. 1, the universal cord 41 extends from a side surface of the grasping portion 33. The universal cord 41 is connected to a control apparatus (not shown).

[Internal Configuration of Operation Portion 30]

The internal Configuration of the operation portion 30 will be described below.

[Plate Member 50]

As shown in FIGS. 3A, 3B, 3C, and 3D, the endoscope 10 includes a plate member 50 which is fixed an inside of the operation portion 30, to which a member 43 that is operated to bend the bendable portion 23 of the endoscope 10 is fixed the plate member 50, and which is formed in a plate shape. The member 43 includes, for example, a bending mechanism of the bending operation portion 37. This bending mechanism includes, for example, a pulley and the like coupled to an operation wire (not shown) and the bending operation portion 37. The operation wire is coupled to the bendable portion 23.

The plate member 50 is formed from a hard member to ensure the strength of the plate member 50. The plate member 50 is formed from, for example, a metal member such as a stainless steel member. The plate member 50 has, for example, a rectangular shape.

As shown in FIGS. 3A, 3B, 3C, and 3D, the plate member 50 includes an obverse surface 51a on which the member 43 is disposed, a reverse surface 51b, a distal end portion 50a, and a proximal end portion (not shown). The plate member 50 is covered by a holding casing (not shown) disposed on the grasping portion 33 except for the distal end portion 50a.

Figure 3A:
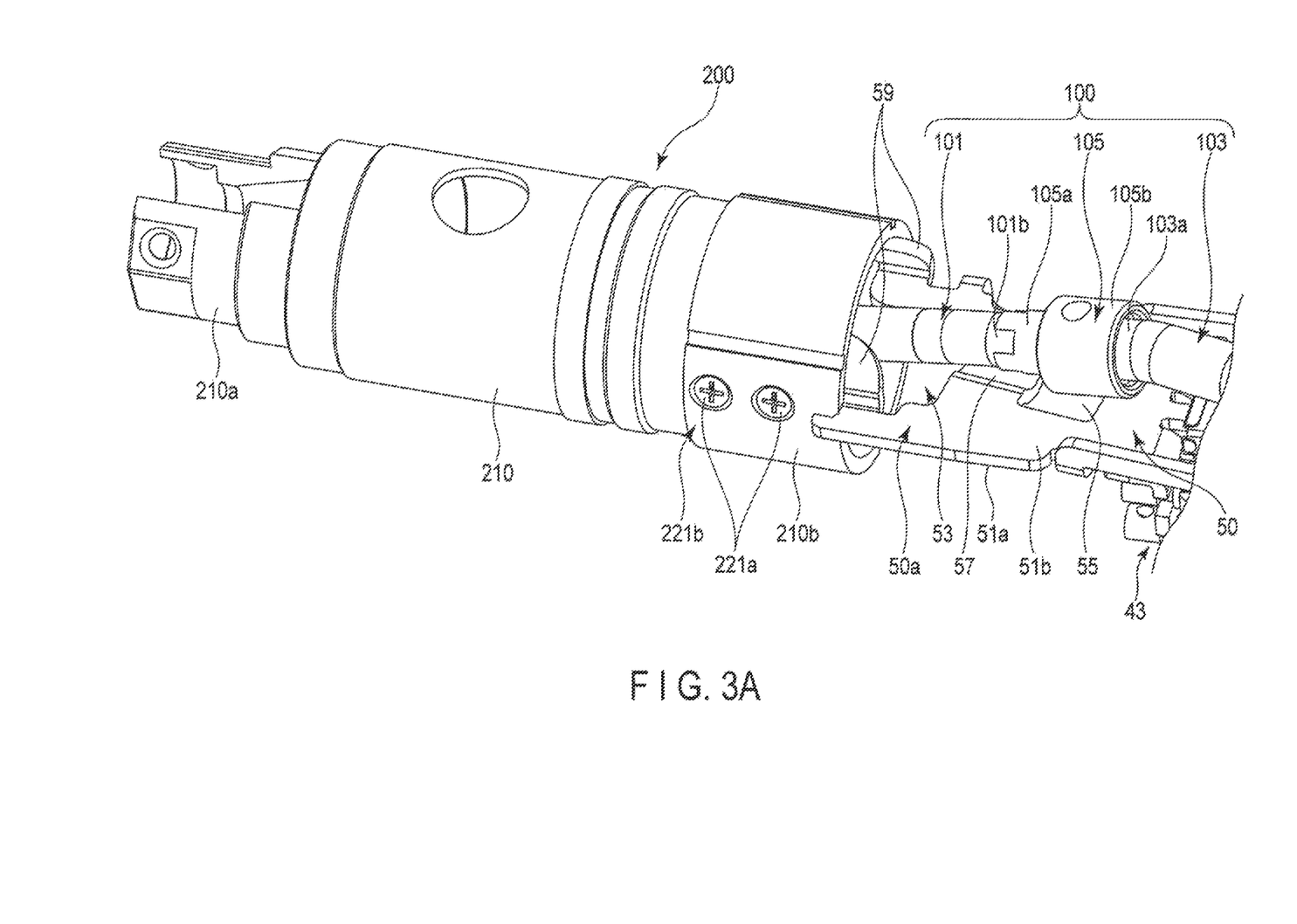
FIG. 3A is a perspective view of peripheral portions of a main body member when viewed from a reverse surface side of a plate member.

As shown in FIG. 3A, the distal end portion 50a is bifurcated to dispose a lengthwise-direction recess portion 53 recessed from the distal end portion 50a toward the proximal end portion of the plate member 50 in a lengthwise direction of the plate member 50. The lengthwise-direction recess portion 53 penetrates through the plate member 50 in a thickness direction of the plate member 50. The lengthwise-direction recess portion 53 is interposed between the bifurcated portions of the distal end portion 50a in a widthwise direction of the plate member 50.

As shown in FIGS. 3A, 3B, 3C, and 3D, the plate member 50 further includes a through hole 55 penetrating through the plate member 50 in the thickness direction of the plate member 50 and a thickness-direction recess portion 57 formed by being recessing a portion of the plate member 50 as a whole from the reverse surface 51b toward the obverse surface 51a in the thickness direction of the plate member 50.

As shown in FIG. 3A, the through hole 55 is disposed in the distal end portion 50a of the plate member 50, more specifically, is disposed between the lengthwise-direction recess portion 53 and the proximal end portion of the plate member 50 in the lengthwise direction of the plate member 50. The through hole 55 is coaxially disposed with respect to the lengthwise-direction recess portion 53 in the lengthwise direction of the plate member 50. A width of the through hole 55 is shorter than that of the lengthwise-direction recess portion 53. The through hole 55 has, for example, a rectangular shape.

Figure 3B:
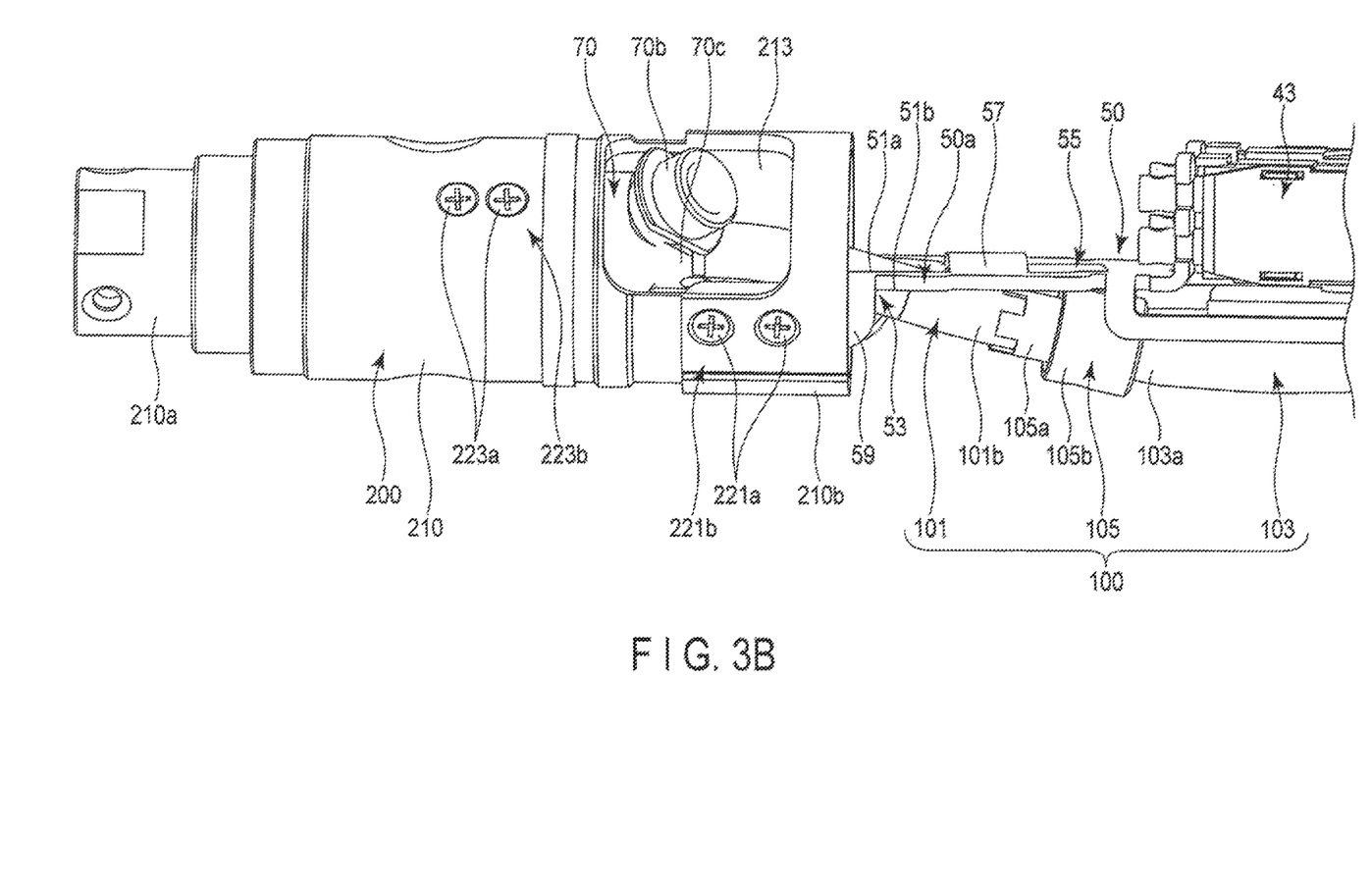
FIG. 3B is a view of the peripheral portions of the main body member when viewed from a side of the plate member.
Figure 3C:
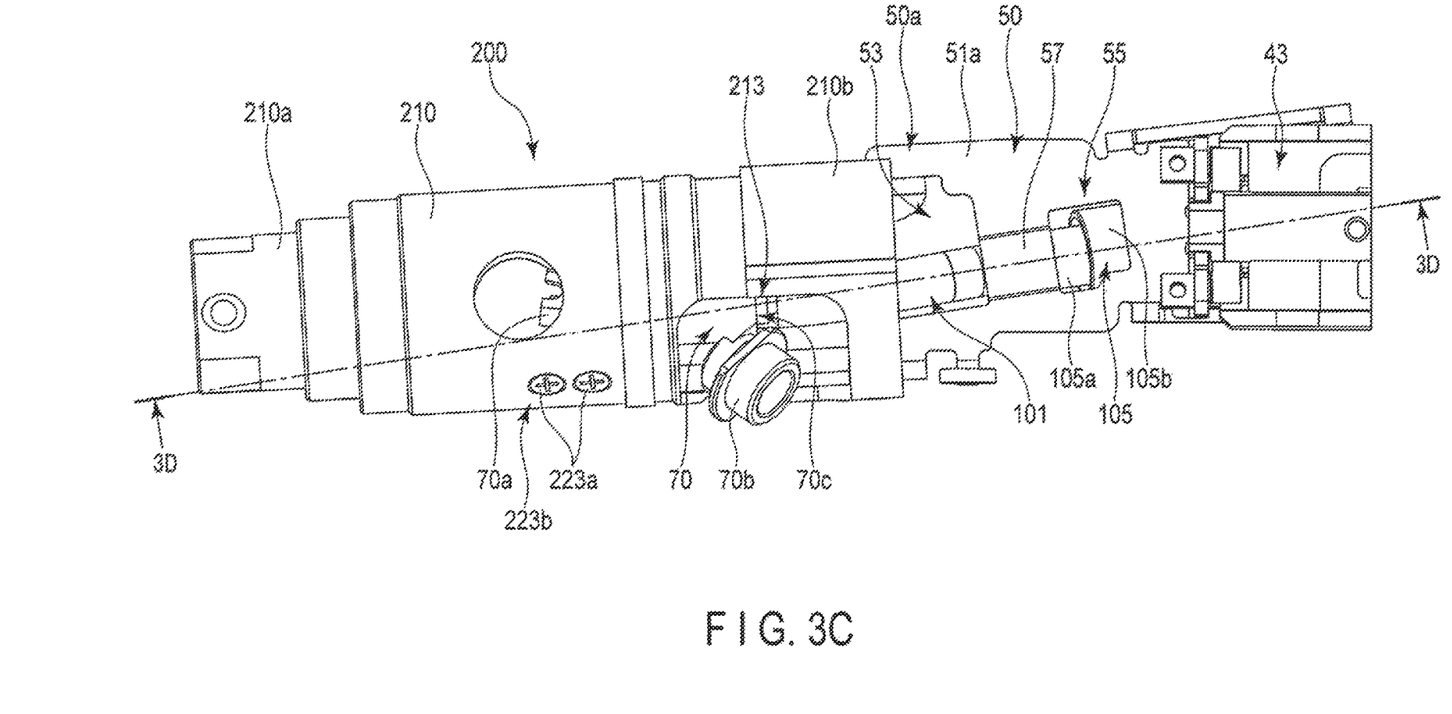
FIG. 3C is a top view of the peripheral portions of the main body member when viewed from an obverse surface side of the plate member.

As shown in FIGS. 3A and 3B, the thickness-direction recess portion 57 is formed by, for example, a press such that a part forming the thickness-direction recess portion 57 has the same thickness as that of the plate member 50. As described above, the thickness-direction recess portion 57 is not formed by scraping only the reverse surface 51b. As shown in FIGS. 3A and 3C, for example, the thickness-direction recess portion 57 has a width almost equal to that of the through hole 55.

As shown in FIG. 3A, the thickness-direction recess portion 57 is disposed between the lengthwise-direction recess portion 53 and the through hole 55 in the lengthwise direction of the plate member 50. The thickness-direction recess portion 57 is disposed adjacent to the lengthwise-direction recess portion 53 and the through hole 55 in the lengthwise direction of the plate member 50. The lengthwise-direction recess portion 53, the through hole 55, and the thickness-direction recess portion 57 described above are disposed on the path of a hard tubular member 101 of a tubular unit 100 (to be described later). The thickness-direction recess portion 57 has an inner shape conforming to an outer shape of a mouth ring member 105a of a coupling portion 105 (to be described later). The coupling portion 105 is disposed as a protruding portion of a proximal end portion 101b of the hard tubular member 101 of the tubular unit 100 (to be described later).

[Branched Tube Member 70, Treatment Instrument Insertion Tube Portion 80, Mouth Ring Portion 90, and Tubular Unit 100]

Figure 2:
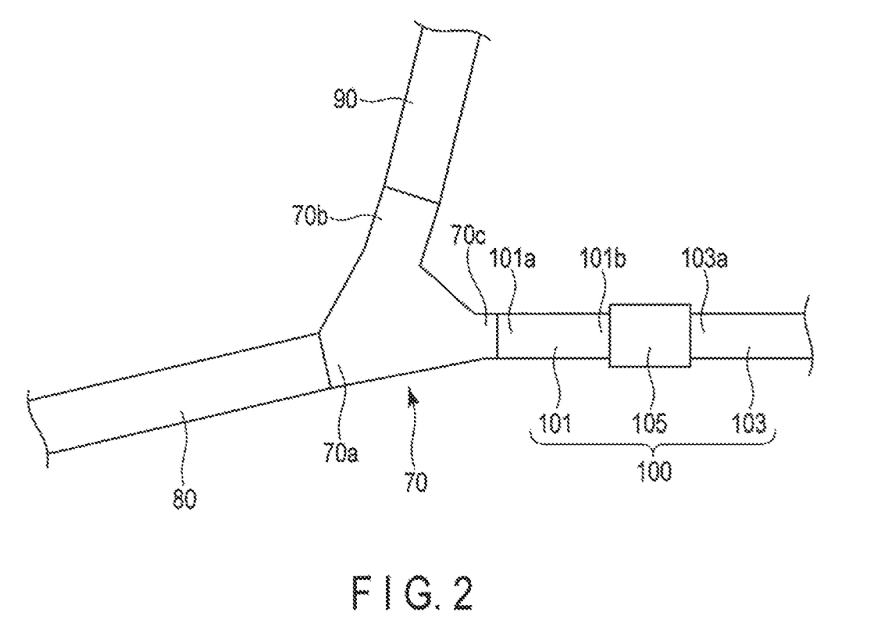
FIG. 2 is a simple view of a positional relationship between a branched tube member, a treatment instrument insertion tube portion, a mouth ring member, a hard tubular member, a soft tubular member, and a coupling portion.

As shown in FIG. 2, the endoscope 10 further includes a branched tube member 70 having one distal end portion 70a and two proximal end portions 70b and 70c formed in a bifurcated shape and a treatment instrument insertion tube portion 80 coupled to the distal end portion 70a of the branched tube member 70. The endoscope 10 further includes a mouth ring portion 90 coupled to the first proximal end portion 70b of the branched tube member 70 and formed a path to the treatment instrument insertion port portion 35a and the tubular unit 100 coupled to the second proximal end portion 70c of the branched tube member 70.

As shown in FIG. 2, the branched tube member 70, the treatment instrument insertion tube portion 80, the mouth ring portion 90, and the tubular unit 100 are discrete from each other. The branched tube member 70, the treatment instrument insertion tube portion 80, the mouth ring portion 90, and the tubular unit 100 are formed as tubular members. The branched tube member 70 and the mouth ring portion 90 are formed from hard members such as metal members.

The branched tube member 70, the treatment instrument insertion tube portion 80, and the mouth ring portion 90 are disposed on the obverse surface 51a side. For the sake of illustrative simplicity, FIG. 3B shows that the treatment instrument insertion tube portion 80 is disposed on the obverse surface 51a side. More specifically, the branched tube member 70, the treatment instrument insertion tube portion 80, and the mouth ring portion 90 are disposed ahead of the distal end portion 50a of the plate member 50 so as to be disposed on a plane on which the obverse surface 51a is disposed. The tubular unit 100 extends from this plane side to the reverse surface 51b side of the plate member 50 through the lengthwise-direction recess portion 53 disposed in the distal end of the plate member 50. More specifically, the tubular unit 100 is disposed on a plane on which the reverse surface 51b is disposed. As described above, the branched tube member 70, the treatment instrument insertion tube portion 80, and the mouth ring portion 90 are disposed on the opposite side of the plate member 50 to the tubular unit 100.

As shown in FIG. 2, the branched tube member 70 is coupled to the treatment instrument insertion tube portion 80 and the mouth ring portion 90 so as to make the treatment instrument insertion tube portion 80 and the mouth ring portion 90 communicate with the branched tube member 70 and make a treatment instrument inserted into the mouth ring portion 90 travel to the treatment instrument insertion tube portion 80.

As shown in FIG. 2, the branched tube member 70 is coupled to the treatment instrument insertion tube portion 80 and the tubular unit 100 so as to make the treatment instrument insertion tube portion 80 and the tubular unit 100 communicate with the branched tube member 70 and make a fluid travel from the treatment instrument insertion tube portion 80 to the tubular unit 100. The fluid includes a gas or liquid mixed with a solid.

In this manner, the branched tube member 70, the treatment instrument insertion tube portion 80, and the tubular unit 100 function as flow channel members in which, for example, the fluid flows and which transport the fluid. The flow channel members run on the reverse surface 51b side of the plate member 50 at a soft tubular member 103 (to be described later) of the tubular unit 100, shift and run from the reverse surface 51b of the plate member 50 to the obverse surface 51a side through the hard tubular member 101 (to be described later) of the tubular unit 100, and run on the obverse surface 51a side of the plate member 50 at the branched tube member 70 and the treatment instrument insertion tube portion 80.

The treatment instrument insertion tube portion 80 is formed from a soft member such as a resin member. The treatment instrument insertion tube portion 80 is disposed an inside of the insertion portion 20 and extends from the flexible tube portion 25 to the distal hard portion 21 through the bendable portion 23. A distal end portion of the treatment instrument insertion tube portion 80 communicates with a distal end opening portion (not shown) disposed in the distal hard portion 21.

The mouth ring portion 90 communicates with the treatment instrument insertion port portion 35a.

[Tubular Unit 100]

As described above, the fluid flows in the tubular unit 100, and the tubular unit 100 transports the fluid. The tubular unit 100 is formed in a tubular shape to allow the fluid to flow in the tubular unit 100. As shown in FIGS. 2, 3A, 3B, 3C, and 3D, the tubular unit 100 includes a tubular member with hardness (to be referred to as the hard tubular member 101 hereinafter) and a tubular member with softness (to be referred to as the soft tubular member 103 hereinafter). The hard tubular member 101 includes a distal end portion 101a coupled to the second proximal end portion 70c of the branched tube member 70 and the proximal end portion 101b. The soft tubular member 103 includes a distal end portion 103a coupled to the proximal end portion 101b of the hard tubular member 101 and a proximal end portion (not shown). The tubular unit 100 further includes the coupling portion 105 which couples the proximal end portion 101b of the hard tubular member 101 and the distal end portion 103a of the soft tubular member 103 to each other so as to make the hard tubular member 101 communicate with the soft tubular member 103. The coupling portion 105 functions as a protruding portion which protrudes from an outer surface of the tubular unit 100 toward an outside of the tubular unit 100, and is disposed as the protruding portion on the tubular unit 100.

[Hard Tubular Member 101]

The hard tubular member 101 is formed from a hard member such as a metal member. The hard tubular member 101 is almost linearly disposed in the lengthwise direction of the plate member 50.

Figure 3D:
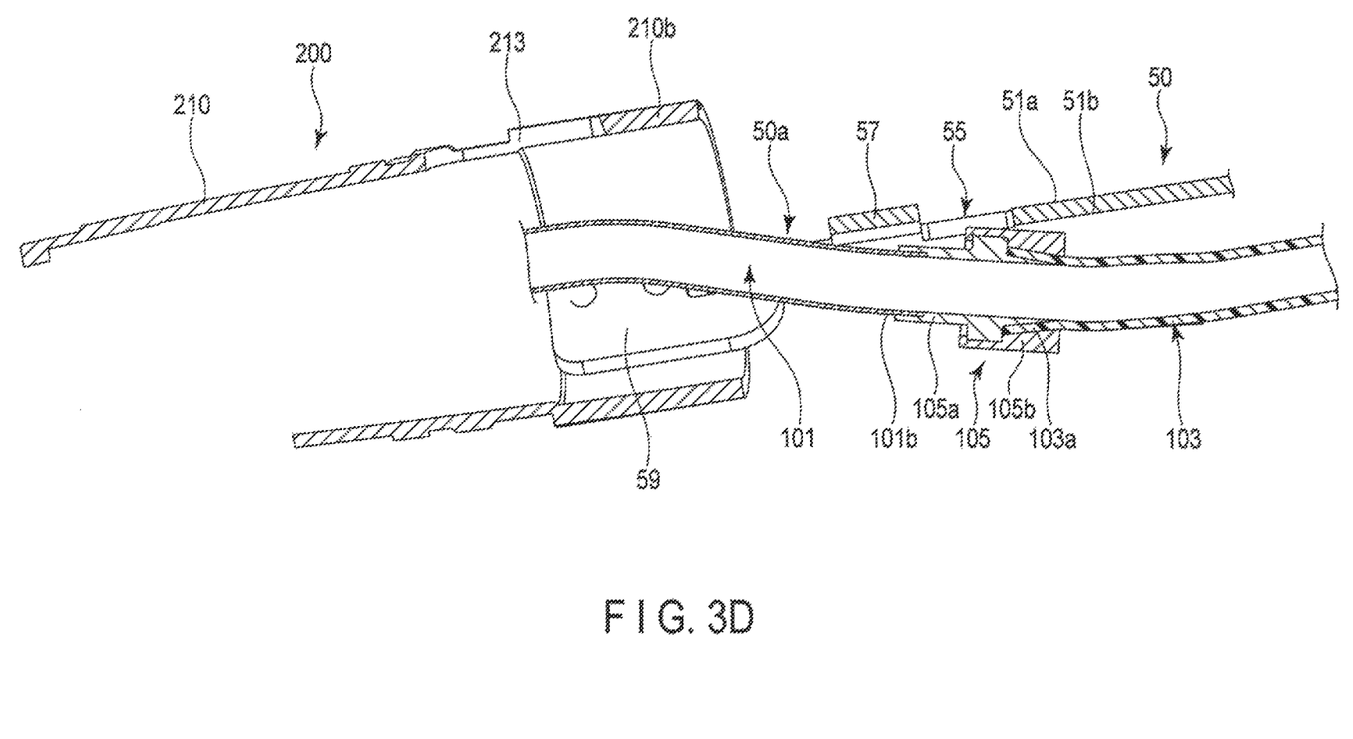
FIG. 3D is a sectional view taken along a line 3D-3D shown in FIG. 3C, showing the disposed state of the hard tubular member and the positional relationship between the hard tubular member, a lengthwise-direction recess portion, a thickness-direction recess portion, the coupling portion, and a through hole.

As shown in FIGS. 3A, 3B, 3C, and 3D, the hard tubular member 101 extends from the plane side on which the obverse surface 51a of the plate member 50 is disposed toward the through hole 55 through the lengthwise-direction recess portion 53 disposed in the distal end of the plate member 50 and the thickness-direction recess portion 57 on the reverse surface 51b side of the plate member 50. As shown in FIGS. 3B and 3D, the hard tubular member 101 gently bends with respect to the thickness direction of the plate member 50 instead of rapidly meandering. Note that the hard tubular member 101 is preferably disposed in an almost linear state along a direction oblique to the thickness direction of the plate member 50. It is preferable that the hard tubular member 101 finely bend only from the proximal end portion 70c to the lengthwise-direction recess portion 53, and extend linearly from the lengthwise-direction recess portion 53 to the through hole 55. More specifically, when a cleaning tool such as a cleaning brush is inserted from, for example, the tubular unit 100 into the treatment instrument insertion tube portion 80 through the branched tube member 70 to clean, for example, the treatment instrument insertion tube portion 80, the branched tube member 70, and the tubular unit 100, the hard tubular member 101 is disposed so as to make a moving direction and axial direction of the cleaning tool almost coincide with a axial direction of the hard tubular member 101 without making the cleaning tool abut against the hard tubular member 101. This prevents the cleaning tool from abutting against the hard tubular member 101, thus preventing the wear of the hard tubular member 101 which is caused by abutment. With the above operation, the hard tubular member 101 is efficiently cleaned in a short period of time.

Note that if the hard tubular member 101 bends while rapidly meandering, the cleaning tool abuts against the hard tubular member 101. With this abutment, the hard tubular member 101 wears. The cleaning tool cannot efficiently clean the hard tubular member 101, thus taking much time for cleaning. In this embodiment, however, since the hard tubular member 101 is disposed in the above manner, this drawback can be overcome.

Since the hard tubular member 101 is hard, the shape of the hard tubular member 101 disposed in the above manner is defined. This prevents the hard tubular member 101 from being bent by an external force, even if the cleaning tool abuts against the hard tubular member 101, the deformation of the hard tubular member 101 accompanying the abutment is prevented.

[Soft Tubular Member 103]

The soft tubular member 103 is disposed on the reverse surface 51b side of the plate member 50. The soft tubular member 103 is formed from a soft member such as a resin member. A proximal end portion of the soft tubular member 103 is connected to, for example, the suction switch 39a or the air-supply/water-supply switch 39b.

[Coupling Portion 105]

As shown in FIGS. 3A, 3B, 3C, and 3D, the coupling portion 105 includes the mouth ring member 105a which is disposed on the proximal end portion 101b of the hard tubular member 101, and a nut member 105b which covers the distal end portion 103a of the soft tubular member 103 covering the mouth ring member 105a and fastens the distal end portion 103a of the soft tubular member 103. The nut member 105b rotates around the axis of the nut member 105b to fasten the soft tubular member 103. This couples the soft tubular member 103 to the hard tubular member 101 through the mouth ring member 105a. The nut member 105b is discrete from the tubular unit 100, the mouth ring member 105a may be integral with or discrete from the tubular unit 100.

An inner diameter of the mouth ring member 105a is almost equal to that of the hard tubular member 101, an outer diameter of the mouth ring member 105a is larger than that of the hard tubular member 101. An outer diameter of the nut member 105b is larger than that of the soft tubular member 103. As described above, the coupling portion 105 is disposed on the tubular unit 100 and protrudes from the outer surface of the tubular unit 100 toward the outside. The coupling portion 105 is disposed on a portion of the tubular unit 100. The mouth ring member 105a is a portion of the coupling portion 105 (protruding portion), and the nut member 105b is another portion of the coupling portion 105 (protruding portion).

As shown in FIG. 3A, a width of the mouth ring member 105a is smaller than that of the through hole 55 and that of the thickness-direction recess portion 57, and a width of the nut member 105b is larger than that of the through hole 55.

[Positioning Mechanism 200]

As shown in FIGS. 3A, 3B, 3C, and 3D, the endoscope 10 further includes a positioning mechanism 200 which positions the plate member 50 and the branched tube member 70 relative to each other. The positioning mechanism 200 includes a cylindrical main body member 210 into which the branched tube member 70 and the treatment instrument insertion tube portion 80 are inserted, and which the mouth ring portion 90 and the tubular unit 100 protrude from an inside of the main body member 210 to an outside of the main body member 210, and fixing members 221a and 223a which fix the plate member 50 and the branched tube member 70 to the main body member 210 while the plate member 50 and the branched tube member 70 are positioned relative to each other. The positioning mechanism 200 is disposed between the bending prevention portion 31, which prevents rapid bending of the flexible tube portion 25, and the grasping portion 33 grasped by the operator who operates the endoscope 10. For this reason, the main body member 210 includes a distal end portion 210a on which the proximal end portion of the bending prevention portion 31 is externally mounted, and a proximal end portion 210b on which the distal end portion of a cylindrical holding casing (not shown) disposed on the grasping portion 33 is externally mounted. As described above, the main body member 210 also serves as a coupling portion which couples the bending prevention portion 31 and the grasping portion 33 to each other.

As shown in FIG. 3B, the main body member 210 includes an opening portion 213 to which the exterior casing of the treatment instrument insertion portion 35 is attached. The opening portion 213 is disposed in a portion of the circumferential surface of the main body member 210 to make the inside and outside of the main body member 210 communicate with each other. The opening portion 213 is disposed in the proximal end portion 210*b* of the main body member 210. The opening portion 213 has a rectangular shape.

The plate member 50 and the branched tube member 70 are fixed to the main body member 210. The fixing of the plate member 50 to the main body member 210 and the fixing of the branched tube member 70 to the main body member 210 will be described below.

[Fixing of Plate Member 50 to Main Body Member 210]

As shown in FIGS. 3A, 3B, 3C, and 3D, in the distal end portion 50*a* of the plate member 50, which is bifurcated, the distal end portion 50*a* has bent portions 59 which bend from the widthwise direction of the plate member 50 to the thickness direction. The bent portions 59 are disposed on the reverse surface 51*b* side. The bent portions 59 face each other in the widthwise direction of the plate member 50. The bent portions 59 are formed along an inner surface of the main body member 210.

As shown in FIGS. 3A, 3B, 3C, and 3D, the bent portions 59 are inserted from the proximal end portion 210*b* of the main body member 210 into the main body member 210. The bent portions 59 are fixed to the proximal end portion 210*b* of the main body member 210 with the fixing members 221*a* such as screws while abutting against the inner surface of the main body member 210.

As shown in FIGS. 3A and 3B, an attachment position 221*b* of the plate member 50 with respect to the main body member 210 is disposed on the proximal end portion 210*b* of the main body member 210 such that the lengthwise-direction recess portion 53, the thickness-direction recess portion 57, and the through hole 55 are disposed in the outside of the main body member 210. The attachment position 221*b* is adjacent to a proximal end portion of the opening portion 213 in a circumferential direction of the main body member 210.

The plate member 50 fixed to the main body member 210 is covered by a holding casing. The plate member 50 is fixed to the main body member 210 with the bent portions 59 and the fixing members 221*a*, thereby the plate member 50 is disposed the inside of the operation portion 30.

In this manner, the plate member 50 is directly fixed to the main body member 210.

[Fixing of Branched Tube Member 70 to Main Body Member 210]

For example, the branched tube member 70 is attached to the main body member 210 before the plate member 50 is attached to the main body member 210. The distal end portion 70*a* of the branched tube member 70 including the treatment instrument insertion tube portion 80 is inserted from the proximal end portion 210*b* of the main body member 210 into the main body member 210. As shown in FIGS. 3B and 3C, the branched tube member 70 is fixed to the distal end portion 210*a* side of the main body member 210 with the fixing members 223*a* such as screws while abutting against the inner surface of the main body member 210.

As shown in FIGS. 3B and 3C, an attachment position 223*b* of the branched tube member 70 with respect to the main body member 210 is adjacent to, for example, the opening portion 213 in the axial direction of the main body member 210, and is located ahead of the opening portion 213. The attachment position 223*b* is shifted from the attachment position 221*b* in the circumferential direction of the main body member 210.

The branched tube member 70 is fixed to the main body member 210 in this manner, thereby the tubular unit 100 is fixed to the main body member 210 through the branched tube member 70.

[Positioning of Plate Member 50 and Branched Tube Member 70 Relative to Main Body Member 210]

When the plate member 50 and the branched tube member 70 are fixed to the main body member 210 in the above manner, the plate member 50 and the branched tube member 70 need to be fixed while being positioned relative to each other based on the positional relationship between the bending operation portion 37 and the treatment instrument insertion port portion 35*a*. This point will be described below.

In general, the bending operation portion 37 is operated with the left hand while grasping the endoscope 10 with the left hand. At this time, the treatment instrument inserted from the treatment instrument insertion port portion 35*a* into the inside of the endoscope 10 is operated by the right hand. The bending operation portion 37 and the treatment instrument insertion portion 35 including the treatment instrument insertion port portion 35*a* are disposed in consideration of this graspability and two types of operability. More specifically, the bending operation portion 37 is disposed on a right side surface of the endoscope 10 when viewed from the operator who grasps the endoscope 10, while the treatment instrument insertion portion 35 is disposed between the right side surface and a back surface of the endoscope 10 when viewed from the operator. In this manner, the bending operation portion 37 and the treatment instrument insertion portion 35 are positioned relative to each other. For this reason, the positioning mechanism 200 positions the plate member 50 and the branched tube member 70 to each other such that the plate member 50 on which the member 43, which performs bending operation, is disposed and the branched tube member 70 functioning as part of the treatment instrument insertion portion 35 is relatively positioned based on the positional relationship between the bending operation portion 37 and the treatment instrument insertion portion 35*a* described above.

More specifically, as shown in FIGS. 3A, 3B, 3C, and 3D, the positioning mechanism 200 relatively positions the plate member 50 and the branched tube member 70, to which the tubular unit 100 is coupled, such that the first proximal end portion 70*b* of the branched tube member 70 protrudes from the main body member 210 toward the outside of the main body member 210 through the opening portion 213, and the tubular unit 100 extends from the plane side on which the obverse surface 51*a* is disposed toward the through hole 55 through the lengthwise-direction recess portion 53 and the thickness-direction recess portion 57 on the reverse surface 51*b* side.

Along with the above positioning, the opening portion 213 is also disposed. More specifically, as shown in FIG. 3B, while the plate member 50 is attached to the main body member 210, the opening portion 213 is formed between a plane including the plate member 50 and a plane perpendicular to this plane. In other words, the opening portion 213 is formed between a side surface of the plate member 50 and an upper side of the obverse surface 51*a* of the plate member 50. As described above, the opening portion 213 is not squarely facing the plate member 50.

The above positioning operation alone may lead to an increase in the thickness of the cylindrical main body member 210, this may lead to an increase in the thickness of the operation portion 30. The operation portion 30 needs to be thinned in consideration of, for example, the graspability of the operation portion 30.

The space inside of the operation portion 30 is limited. If, therefore, the hard tubular member 101, the soft tubular member 103, and the coupling portion 105 are greatly separated from the plate member 50 in the thickness direction of the plate member 50, a component to be built in the operation portion 30 may not be accommodated in the space.

In order to prevent an increase in the thickness of the main body member 210, the coupling portion 105 may be placed closer to the plate member 50. In this case, however, the coupling portion 105 does not easily rotate, and hence the hard tubular member 101 may not be easily coupled to the soft tubular member 103.

For this reason, the positioning mechanism 200 positions the plate member 50 and the branched tube member 70 including the tubular unit 100 relative to each other so as to ensure the graspability of the operation portion 30, the space inside of the operation portion 30, and the connectivity between the tubular members. More specifically, as shown in FIGS. 3A, 3B, 3C, and 3D, the positioning mechanism 200 positions the plate member 50 and the branched tube member 70 including the tubular unit 100 relative to each other so as to dispose the protruding coupling portion 105 around a periphery of the through hole 55 including the through hole 55. More specifically, as shown in FIG. 3B, the positioning mechanism 200 positions the plate member 50 and the branched tube member 70, to which the tubular unit 100 is coupled, relative to each other such that the coupling portion 105, which is a protruding portion, slightly separate from, for example, the periphery of the through hole 55 including the through hole 55 on the reverse surface 51b of the plate member 50 in the thickness direction of the plate member 50.

As shown in FIGS. 3A, 3B, 3C, and 3D, the positioning mechanism 200 positions the plate member 50 and the branched tube member 70 relative to each other in, for example, the thickness direction of the plate member 50 so as to dispose the proximal end portion 101b of the hard tubular member 101 in the tubular unit 100 and the mouth ring member 105a of the coupling portion 105, which is disposed as a portion of the protruding portion, substantially coaxially with respect to the thickness-direction recess portion 57 in the thickness direction of the plate member 50. More specifically, the positioning mechanism 200 positions the plate member 50 and the branched tube member 70 relative to each other in the thickness direction of the plate member 50 such that the proximal end portion of the hard tubular member 101 and the mouth ring member 105a are disposed so as to be lifted and separated from the plate member 50 including the thickness-direction recess portion 57 on the reverse surface 51b, in other words, a gap portion is formed between the inside of the thickness-direction recess portion 57 and both the proximal end portion 101b of the hard tubular member 101 and the mouth ring member 105a. In this manner, as shown in FIGS. 3A, 3B, and 3D, the positioning mechanism 200 positions the plate member 50 and the branched tube member 70 relative to each other so as to dispose the proximal end portion 101b of the hard tubular member 101 and the mouth ring member 105a while preventing them from interfering with and abutting against the plate member 50 including the thickness-direction recess portion 57.

As shown in FIG. 3B, according to the above description, the tilts of the proximal end portion 101b of the hard tubular member 101 and the mouth ring member 105a with respect to the plate member 50 with the disposition of the lengthwise-direction recess portion 53 and the thickness-direction recess portion 57 are gentler than those without the disposition of the lengthwise-direction recess portion 53 and the thickness-direction recess portion 57. In other words, the proximal end portion 101b of the hard tubular member 101 and the mouth ring member 105a with the formation of the lengthwise-direction recess portion 53 and the thickness-direction recess portion 57 are disposed closer to the plate member 50 than without the disposition of the lengthwise-direction recess portion 53 and the thickness-direction recess portion 57. In other words, the proximal end portion 101b of the hard tubular member 101 and the mouth ring member 105a are disposed almost along the plate member 50.

As shown in FIGS. 3A, 3B, 3C, and 3D, the positioning mechanism 200 positions the plate member 50 and the branched tube member 70 relative to each other so as to dispose, for example, the nut member 105b of the coupling portion 105 disposed as another portion of the protruding portion almost coaxially with respect to, for example, the through hole 55 in the thickness direction of the plate member 50. The nut member 105b is a portion different from a portion of the protruding portion which is disposed substantially coaxially with respect to the thickness-direction recess portion 57. More specifically, the positioning mechanism 200 positions the plate member 50 and the branched tube member 70 relative to each other in the thickness direction of the plate member 50 such that, for example, the nut member 105b of the coupling portion 105 which is disposed as another portion of the protruding portion is disposed so as to be lifted and separated from the plate member 50 including the through hole 55, in other words, a gap portion is formed between the nut member 105b and the through hole 55. Note that in this embodiment, as shown in FIG. 3D, in the nut member 105b of the coupling portion 105 which is disposed as another portion of the protruding portion, the positioning mechanism 200 may position the plate member 50 and the branched tube member 70 relative to each other such that a portion of the nut member 105b is inserted into (disposed close to) the through hole 55. As described above, as shown in FIGS. 3A, 3B, and 3D, the positioning mechanism 200 positions the plate member 50 and the branched tube member 70 relative to each other so as to prevent the nut member 105b from interfering with and abutting against the plate member 50 including the through hole 55.

As shown in FIGS. 3B, 3C, and 3D, according to the above description, while the plate member 50 and the branched tube member 70 are fixed to the main body member 210, since the hard tubular member 101 is coupled to the soft tubular member 103, it is possible to operate the coupling portion 105 from either the reverse surface 51b side or the obverse surface 51a side through the through hole 55. This operation includes, for example, fastening the nut member 105b.

[Function]

As shown in FIGS. 3A, 3B, 3C, and 3D, in this embodiment, the positioning mechanism 200 positions the plate member 50 and the branched tube member 70 including the tubular unit 100 relative to each other so as to dispose the protruding coupling portion 105 around the through hole 55 including the through hole 55. More specifically, as shown in FIG. 3B, the positioning mechanism 200 positions the plate member 50 and the branched tube member 70, to which the tubular unit 100 is coupled, relative to each other so as to slightly separate the coupling portion 105, which is the protruding portion, from, for example, the periphery of the through hole 55 including the through hole 55 on the reverse surface 51b of the plate member 50 in the thickness direction of the plate member 50. This prevents an increase in the thickness of the main body member 210, and prevents the hard tubular member 101, the soft tubular member 103, and the coupling portion 105 from greatly separating from the plate member 50 in the thickness direction of the plate member 50, therefore, the component to be built in the operation portion 30 is accommodated in the space. In this manner, the graspability of the operation portion 30 and the space inside of the operation portion 30 are ensured. The coupling portion 105 easily rotates to allow the hard tubular member 101 to be easily coupled to the soft tubular member 103. In this manner, the connectivity between the tubular members is ensured.

As shown in FIGS. 3A, 3B, 3C, and 3D, the positioning mechanism 200 positions the plate member 50 and the branched tube member 70 relative to each other so as to dispose, for example, the proximal end portion 101b of the hard tubular member 101 in the tubular unit 100 and the mouth ring member 105a of the coupling portion 105, which is disposed as a portion of the protruding portion, almost axially with respect to the thickness-direction recess portion 57 in the thickness direction of the plate member 50. More specifically, the positioning mechanism 200 positions the plate member 50 and the branched tube member 70 relative to each other such that the proximal end portion of the hard tubular member 101 and the mouth ring member 105a are lifted and separated from the plate member 50 including the thickness-direction recess portion 57 on the reverse surface 51b side, and the gap portion is formed between the inside of the thickness-direction recess portion 57 and both the proximal end portion of the hard tubular member 101 and the mouth ring member 105a.

This prevents an increase in the thickness of the main body member 210, and prevents the hard tubular member 101, the soft tubular member 103, and the coupling portion 105 from greatly separating from the plate member 50 in the thickness direction of the plate member 50, therefore, the component to be built in the operation portion 30 is accommodated in the space. In this manner, the graspability of the operation portion 30 and the space inside of the operation portion 30 are ensured.

With the above arrangement, the hard tubular member 101 and the mouth ring member 105a are disposed so as not to interfere with and abut against the plate member 50 including the thickness-direction recess portion 57, and are disposed below the thickness-direction recess portion 57. This therefore prevents the proximal end portion 101b of the hard tubular member 101 and the mouth ring member 105a from abutting against the plate member 50, thus preventing wear between them which is caused by abutment.

As shown in FIGS. 3A, 3B, 3C, and 3D, the positioning mechanism 200 positions the plate member 50 and the branched tube member 70 relative to each other so as to dispose, for example, the nut member 105b of the coupling portion 105, which is disposed as another portion of the protruding portion, almost coaxially with respect to, for example, the through hole 55 in the thickness direction of the plate member 50. More specifically, the positioning mechanism 200 positions the plate member 50 and the branched tube member 70 relative to each other such that, for example, the nut member 105b is lifted and separated from the plate member 50 including the through hole 55, and the gap portion is formed between the nut member 105b and the through hole 55.

Even when, therefore, the coupling portion 105 approaches the plate member 50, since the through hole 55 is disposed, the nut member 105b easily rotates to allow the hard tubular member 101 to be easily coupled to the soft tubular member 103. The connectivity between the tubular members is ensured in this manner.

It is possible to operate the nut member 105b from either the reverse surface 51b side or the obverse surface 51a side through the through hole 55.

With the above arrangement, the nut member 105b is disposed so as not to interfere with and abut against the plate member 50 including the through hole 55, and is disposed in an outside of the through hole 55 and below the through hole 55. This therefore prevents the nut member 105b from abutting against the plate member 50, thus preventing wear between them which is caused by abutment.

As described above, since the lengthwise-direction recess portion 53 and the thickness-direction recess portion 57 are disposed, the hard tubular member 101 can be disposed almost linearly along a direction oblique to the thickness direction of the plate member 50 while gently bending instead of rapidly meandering. When, therefore, cleaning the hard tubular member 101 with the cleaning tool such as the cleaning brush, the moving direction and axial direction of the cleaning tool can be made to almost coincide with the axial direction of the hard tubular member 101. This prevents the cleaning tool from abutting against the hard tubular member 101, and hence prevents the wear of the hard tubular member 101 which is caused by abutment. This in turn reduces the replacement frequency of the hard tubular member 101 and prolongs the service life of the hard tubular member 101. The hard tubular member 101 is efficiently cleaned in a short period of time. Since the cleaning tool is prevented from abutting against the hard tubular member 101, the deformation of the hard tubular member 101 accompanying abutment is prevented.

Since the hard tubular member 101 is hard, the shape of the hard tubular member 101 disposed as described above is defined. This prevents the hard tubular member 101 from being bent by an external force and the like, and prevents the deformation of the hard tubular member 101 accompanying abutment even if the cleaning tool abuts against the hard tubular member 101.

[Effect]

As described above, in this embodiment, as shown in FIGS. 3A, 3B, 3C, and 3D, the positioning mechanism 200 positions the plate member 50 and the branched tube member 70 including the tubular unit 100 relative to each other so as to dispose the protruding portion around the periphery of the through hole 55 including the through hole 55. In the embodiment, this can prevent an increase in the thickness of the main body member 210. In the embodiment, it is possible to prevent the hard tubular member 101, the soft tubular member 103, and the coupling portion 105 from greatly separating from the plate member 50 in the thickness direction of the plate member 50, and hence to accommodate the component to be built in the operation portion 30 in the space. As described above, in the embodiment, it is possible to ensure the graspability of the operation portion 30 and the space inside of the operation portion 30. In the embodiment, it is possible to easily rotate the nut member 105b, thus easily coupling the hard tubular member 101 to the soft tubular member 103. As described above, in the embodiment, it is possible to ensure connectivity between the tubular members.

In this embodiment, as shown in FIGS. 3A, 3B, 3C, and 3D, the positioning mechanism 200 positions the plate member 50 and the branched tube member 70 relative to each other so as to dispose the proximal end portion 101b of the hard tubular member 101 in the tubular unit 100 and the mouth ring member 105a of the coupling portion 105, which is disposed as a portion of the protruding portion, almost coaxially with respect to the thickness-direction recess portion 57 in the thickness direction of the plate member 50. More specifically, the positioning mechanism 200 positions the plate member 50 and the branched tube member 70 relative to each other such that the proximal end portion of the hard tubular member 101 and the mouth ring member 105a are lifted and separated from the plate member 50 including the thickness-direction recess portion 57 on the reverse surface 51b, and the gap portion is formed between the inside of the thickness-direction recess portion 57 and both the proximal end portion of the hard tubular member 101 and the mouth ring member 105a.

In this embodiment, it is possible to reliably prevent the hard tubular member 101, the soft tubular member 103, and the coupling portion 105 from greatly separating from the plate member 50 in the thickness direction of the plate member 50, and to reliably accommodate the component to be built in the operation portion 30 in the space. As described above, in the embodiment, it is possible to reliably ensure the graspability of the operation portion 30 and the space inside of the operation portion 30.

With the above arrangement, in this embodiment, it is possible to prevent the proximal end portion 101b of the hard tubular member 101 and the mouth ring member 105a from abutting against the plate member 50, and hence to prevent wear caused by abutment. In this embodiment, this can reliably prevent an increase in the thickness of the main body member 210.

In this embodiment, as shown in FIGS. 3A, 3B, 3C, and 3D, for example, the positioning mechanism 200 positions the plate member 50 and the branched tube member 70 relative to each other so as to dispose the nut member 105b of the coupling portion 105, which is disposed as another portion of the protruding portion, almost coaxially with respect to, for example, the through hole 55 in the thickness direction of the plate member 50. More specifically, the positioning mechanism 200 positions the plate member 50 and the branched tube member 70 relative to each other such that, for example, the nut member 105b is lifted and separated from the plate member 50 including the through hole 55, and the gap portion is formed between the nut member 105b and the through hole 55.

In this embodiment, this makes it possible to easily rotate the coupling portion 105 and to easily couple the hard tubular member 101 to the soft tubular member 103 because of the disposition of the through hole 55, even if the coupling portion 105 approaches the plate member 50. In the embodiment, the connectivity between the tubular members can be ensured in this manner.

With the above arrangement, as shown in FIGS. 3A, 3B, 3C, and 3D, in this embodiment, it is possible to prevent the nut member 105b from abutting against the plate member 50 and to prevent wear between them which is caused by abutment.

In this embodiment, as shown in FIGS. 3A, 3B, 3C, and 3D, it is possible to operate the nut member 105b from either the reverse surface 51b side or the obverse surface 51a side through the through hole 55.

In this embodiment, as shown in FIGS. 3A, 3B, 3C, and 3D, as described above, since the lengthwise-direction recess portion 53 and the thickness-direction recess portion 57 are disposed, the hard tubular member 101 gently bends, instead of rapidly meandering, and can also be disposed in an almost linear state along the direction oblique to the thickness direction of the plate member 50. When the hard tubular member 101 is cleaned with the cleaning tool such as the cleaning brush, therefore, the moving direction and axial direction of the cleaning tool can be made to almost coincide with the axial direction of the hard tubular member 101. In this embodiment, this makes it possible to prevent the cleaning tool from abutting against the hard tubular member 101, and hence to prevent wear of the hard tubular member 101 which is caused by abutment, this in turn can reduce the replacement frequency of the hard tubular member 101 and prolong the service life of the hard tubular member 101. In the embodiment, the hard tubular member 101 can be efficiently cleaned in a short period of time. In the embodiment, since the cleaning tool can be prevented from abutting against the hard tubular member 101, the deformation of the hard tubular member 101 accompanying abutment can be prevented.

In this embodiment, since the hard tubular member 101 is hard, the shape of the hard tubular member 101 disposed in the above manner can be defined. In the embodiment, this can prevent the hard tubular member 101 from being bent by an external force and the like. Even if the cleaning tool abuts against the hard tubular member 101, the deformation of the hard tubular member 101 accompanying abutment can be prevented.

In this embodiment, only one through hole 55 is disposed to correspond to the mouth ring member 105a. For this reason, in the embodiment, the strength of the plate member 50 can be ensured. In the embodiment, since the plate member 50 is formed from stainless steel, the through hole 55 can be easily formed while the strength of the plate member 50 is ensured. In the embodiment, since the thickness-direction recess portion 57 is disposed, even when the through hole 55 is disposed, the strength of the plate member 50 can be ensured. In this manner, the thickness-direction recess portion 57 can ensure the strength of the plate member 50 of the distal end portion 50a of the plate member 50.

In this embodiment, the branched tube member 70 can be visually recognized from the reverse surface 51b of the plate member 50.

In this embodiment, the through hole 55 is disposed. In the embodiment, this makes it possible to visually recognize through the through hole 55 that the distal end portion 103a of the soft tubular member 103 is covered by the mouth ring member 105a.

In this embodiment, when the branched tube member 70 is fixed to the main body member 210, if the lengthwise-direction recess portion 53 and the thickness-direction recess portion 57 are not disposed, it is difficult for an assembler to intuitively visually recognize the attachment position 223b of the branched tube member 70 with respect to the main body member 210, resulting in much time and effort spent for assembly. In the embodiment, however, the lengthwise-direction recess portion 53 and the thickness-direction recess portion 57 are disposed. If, therefore, the hard tubular member 101 is arranged in correspondence with the lengthwise-direction recess portion 53 and the thickness-direction recess portion 57, it is easy for the assembler to intuitively visually recognize the attachment position 223b of the branched tube member 70 with respect to the main body member 210 and to perform assembly.

Note that in this embodiment, in the nut member 105b of the coupling portion 105 which is disposed as another portion of the protruding portion, the positioning mechanism 200 may position the plate member 50 and the branched tube member 70 relative to each other so as to insert a portion of the nut member 105b into the through hole 55 (disposed near the through hole 55).

In this embodiment, this makes it possible to place the coupling portion 105 closer to the plate member 50 and reliably prevent an increase in the thickness of the main body member 210.

The hard tubular member 101 may be integral with the branched tube member 70.

The through hole 55 may communicate with, for example, the right side of the plate member 50. That is, the through hole 55 may be disposed in the right side surface and recessed from the right side to the left side in the widthwise direction of the plate member, and may function as a notched portion penetrating through the plate member 50 in the thickness direction of the plate member 50.

The present invention is not limited to the embodiment described above, and constituent elements can be modified and embodied in the execution stage within the spirit and scope of the invention. Various inventions can be formed by proper combinations of a plurality of constituent elements disclosed in the above embodiment.

What is claimed is:

1. An endoscope comprising:
   a bendable portion;
   a bender configured to bend the bendable portion;
   a plate member to which the bender is fixed and which includes a through hole;
   a tubular unit including:
      a tubular member with hardness;
      a tubular member with softness; and
      a protruding portion which functions as a coupling portion configured to couple the tubular member with hardness and the tubular member with softness to each other, the protruding portion being disposed so as to protrude from an outer surface of the tubular member with hardness and an outer surface of the tubular member with softness; and
   a positioner configured to position:
      the plate member and the tubular unit relative to each other; and
      a portion of the protruding portion into the through hole;
   wherein:
      the plate member further comprises:
         a thickness-direction recess portion recessed from a back surface of the plate member toward a front surface of the plate member and disposed adjacent to the through hole, and
         a lengthwise-direction recess portion disposed in a distal end portion of the plate member, recessed from the distal end portion toward a proximal end portion of the plate member in a lengthwise direction of the plate member, and penetrating through the plate member, the thickness-direction recess portion being disposed between the lengthwise-direction recess portion and the through hole in the lengthwise direction of the plate member, and
      the positioner is configured to position the plate member and the tubular unit relative to each other such that:
         the tubular unit and the protruding portion do not abut the plate member, and
         the tubular unit extends from a front surface side of the plate member toward the through hole through the lengthwise-direction recess portion and the thickness-direction recess portion on a back surface side of the plate member.

2. The endoscope according to claim 1, further comprising:
   a branched tube member including one distal end portion and two proximal end portions formed in a bifurcated shape;
   a treatment instrument insertion tube portion coupled to the distal end portion of the branched tube member; and
   a mouth ring portion coupled to a first proximal end portion of the branched tube member and formed a path to a treatment instrument insertion port portion,
   wherein:
      the tubular unit is coupled to a second proximal end portion of the branched tube member,
      the positioner further includes:
         a cylindrical main body member into which the branched tube member and the treatment instrument insertion tube portion are inserted and which the mouth ring member and the tubular unit protrude from an inside of the main body member to an outside of the main body member, and
         a fixer configured to fix the plate member and the branched tube member to the main body member while the plate member and the branched tube member are positioned relative to each other,
      the plate member is directly fixed to the main body member, and
      the tubular unit is fixed to the main body member through the branched tube member.

3. The endoscope according to claim 2, wherein the main body member includes:
   a distal end portion on which a proximal end portion of a cylindrical bending prevention portion, from which a flexible tube portion of the endoscope extends, is externally mounted, and
   a proximal end portion on which a distal end portion of a cylindrical holding casing, disposed on a grasper of an operation portion of the endoscope, is externally mounted.

4. The endoscope according to claim 1, wherein the positioner is disposed between a bending prevention portion configured to prevent rapid bending of a flexible tube portion of the endoscope and a grasper configured to be grasped by an operator of the endoscope.

5. The endoscope according to claim 1, wherein the positioner is configured to position the plate member and the tubular unit relative to each other such that a portion of the protruding portion is disposed so as to be separated from the through hole in a thickness direction of the plate member, the portion being different from another portion of the protruding portion that is disposed so as to be separated from the thickness-direction recess portion of the plate member.

* * * * *